United States Patent [19]
Bircoll

[11] Patent Number: 5,868,775
[45] Date of Patent: Feb. 9, 1999

[54] SHAPED BALLOON DISSECTOR AND IMPLANT KIT

[76] Inventor: Melvyn Bircoll, 2700 Casiano Rd., Los Angeles, Calif. 90077

[21] Appl. No.: 953,311

[22] Filed: Oct. 17, 1997

Related U.S. Application Data

[63] Continuation-in-part of Ser. No. 722,472, Sep. 27, 1996, Pat. No. 5,725,545.

[51] Int. Cl.⁶ .................................................. A61B 17/00
[52] U.S. Cl. .......................................... 606/190; 600/207
[58] Field of Search ................................ 606/1, 190, 195; 604/96–101; 623/8, 11; 600/207

[56] References Cited

U.S. PATENT DOCUMENTS

| | | | |
|---|---|---|---|
| 5,669,932 | 9/1997 | Fischell et al. | 606/198 |
| 5,725,545 | 3/1998 | Bircoll | 606/192 |

*Primary Examiner*—William Lewis

[57] ABSTRACT

A kit for use in the surgical implantation of an shaped implant. The kit includes a shaped balloon dissector packaged with an implant which, when inflated, has a shape complimentary with the shape of the dissector. Using orientation indicia for proper orientation, the surgical site is dissected with the shaped balloon dissector. Once so prepared, a shaped deflated implant is positioned within the site and then inflated. Since the implant's shape is complementary with the dissector's shape, the implant fits within the site without requiring excess site preparation.

20 Claims, 8 Drawing Sheets

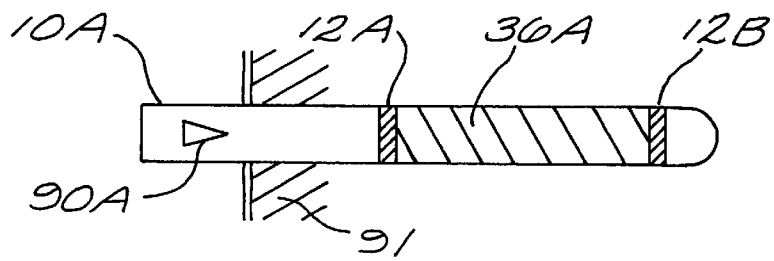
FIG. 9A
FIG. 9B
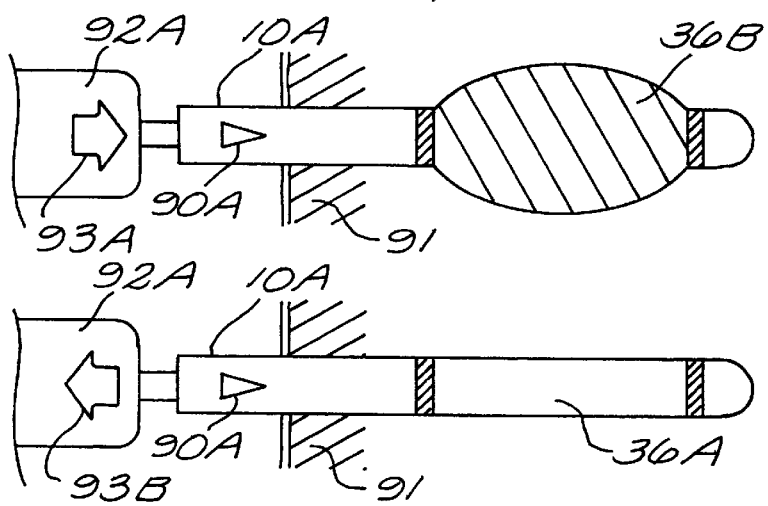
FIG. 9C
FIG. 9D
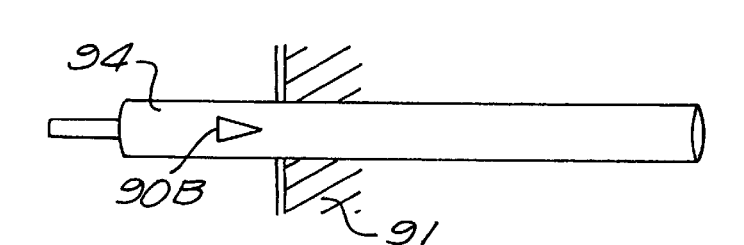
FIG. 9E
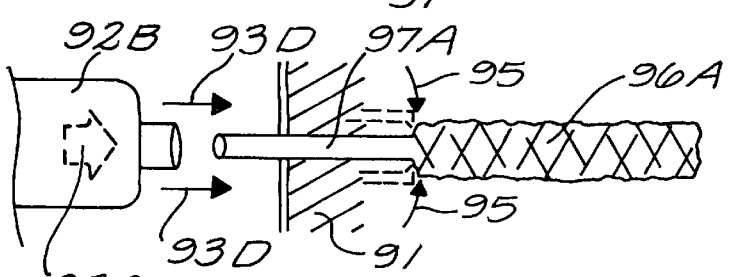
FIG. 9F
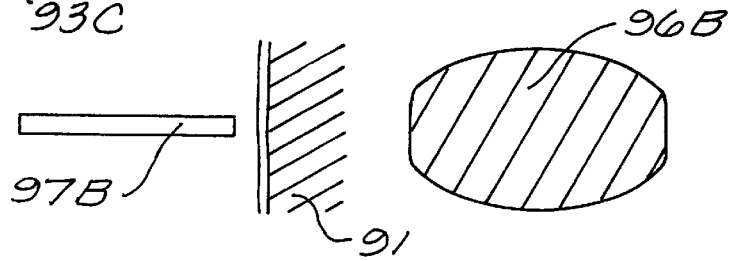

SHAPED BALLOON DISSECTOR AND IMPLANT KIT

BACKGROUND

This is a continuation-in-part of U.S. patent application, Ser. No. 08/722,472, filed Sep. 27, 1996, U.S. Pat. 5,725,545 and entitled "Balloon Dissector".

This invention relates generally to medical devices and more particularly to surgical dissectors used in conjunction with implants.

Dissection is the separation of different structures along natural lines by dividing the connective tissue framework. In a great many surgical procedures, dissection is required to either create a surgical site or to gain access to a specific organ. In practice, dissection is accomplished in one of four different manners: manual; inflation using gas; with a rigid surgical instrument; or through the use of an expandable balloon dissector.

Manual dissection is accomplished when the surgeon uses his/her own fingers as probes to break the connective tissue. This approach is quickly accomplished, but, it requires a large enough incision be made to accept the surgeon's hand. For many procedures, such as plastic surgery, this large incision is counter-productive to the objective of the surgery as an enlarged scar is left after the healing process.

In some applications, such as laparoscopy, a benign gas is injected into the body to inflate a portion, such as the peritoneum, so that surgery using an endoscope can be performed. Although this technique works well with the peritoneum, in most locations within the human body, this technique is not available.

The use of a rigid surgical instrument allows the surgeon to sever the connective tissue. Two types of dissectors are common: the blunt edged; and, the sharp edged. For both of these, the dissector is inserted through an incision and then the surgeon manually moves the dissector so that the connective tissue is cut. While this technique has worked well in most applications, the technique requires a great deal of time and effort in creating the dissection.

Because of all of the above, balloon dissectors have become more widely used. Examples of such dissectors include those described in: U.S. Pat. No. 5,370,134, entitled "Method and Apparatus for Body Structure Manipulation and Dissection" issued to Chin et al. on Dec. 6, 1994; and U.S. Pat. No. 5,549,625, entitled "Balloon Dissector" issued to Bircoll on Aug. 27, 1996. In both of these devices, a sheath is inserted into the site to be dissected and a balloon is exposed from inside the sheath. The balloon is then selectively inflated to dissect the connective tissue.

While the balloon dissection method has some significant advantages, the procedure is somewhat complex and the apparatus itself is relatively costly to manufacture.

It is clear that there is a need for an efficient and easy to use dissector.

SUMMARY OF THE INVENTION

The present invention provides a kit for use in the surgical implantation of a shaped implant.

In this context, a shaped implant includes a variety of implants from silicone implants for the cheeks, to chin implants. The implant, in this context, is an item which is foreign to the patient's body and is intended to modify the patient's body.

To this end, the invention creates a kit for use by the surgeon for the site preparation and placement of the implant. The kit includes a shaped balloon dissector which is packaged with an implant which, when inflated, has a shape complimentary with the shape of the dissector.

The balloon dissector is positioned at the surgical site and is inflated to cause dissection of the site. Once dissection has been accomplished, the balloon dissector is collapsed and removed from the surgical site.

The implant is then inserted into the site. The preferred implant is a collapsible type and is inflated, usually with a benign liquid or gel, once it has been properly positioned; hence, once the collapsed implant has been properly positioned, it is inflated with the liquid or gel to fill the cavity which has been dissected.

The shape of the balloon dissector and the shape of the filled implant are preferably complimentary. This complimentary nature between the two assures that the dissection made and the implant match.

To accomplish this complimentary aspect of the invention, orientation indicia are placed on the handle of the balloon dissector. This indicia is used by the surgeon when the surgical site is dissected with the shaped balloon dissector. The dissection then takes on the shape and orientation desired.

Once so prepared, a shaped deflated implant is positioned within the site and inflated. Proper positioning of the implant is accomplished using an indicia which has been placed on the handle of the implanting apparatus. The implanting apparatus is preferably a hollow tube which includes the implant. The hollow tube is properly positioned using the indicia, and the deflated implant is deposited into the site.

The implanting apparatus, the tube, is withdrawn, leaving the deflated implant to be inflated to fill the site.

Since the implant's shape is complementary with the dissector's shape, the implant fits within the site without requiring excess site preparation.

The invention utilizes a shaped balloon dissector in conjunction with a shaped implant. The shaped balloon dissector of the present invention is an elastic balloon which is positioned on an exterior portion of a rigid tube. The rigid tube is used to both assist in the positioning of the dissecting balloon as well as communication of the inflating medium.

A variety of sizes for the tube are available and are chosen to fit the surgical situation being addressed. The preferred tube (also known as a probe) is approximately $\frac{3}{8}$ of an inch in diameter; This small size allows the probe to be used in a variety of cosmetic surgery applications without requiring an incision which will create a noticeable scar.

In the preferred embodiment, the tube is composed of surgical steel. In an alternative embodiment, the tube is created from rigid plastic; this alternative embodiment is inexpensive to use permitting the dissector of the present invention to become a minor disposable used in the surgical procedure. Another embodiment uses a hardened silicone to form the tube.

In the present invention, an elastic balloon covers a portion of the exterior of the probe/tube. By placing the elastic balloon on an exterior portion of the probe, use of the dissector is vastly simplified since the elastic balloon is ready for use the instant it is positioned, no sheath needs to be removed.

The tube is inserted into the patient and then a medium, such as sterile saline solution or sterile water, is inserted into the hollow tube. While saline is the preferred medium, other liquids and gasses are obvious to those of ordinary skill in the art.

The medium is supplied to the balloon using a variety of mechanisms including: a pump; a bulb; or a syringe. Those of ordinary skill in the art readily recognize a variety of other mechanisms which will serve this function.

The medium is communicated to an interior portion of the elastic balloon causing the balloon to expand and dissect tissue in the area. The medium flows through the tube/probe and exits into the interior of the elastic balloon. The medium forces the elastic balloon to expand.

In many applications, the surgeon is able to check the progress of the balloon's dissecting activity through external monitoring of the patient's body. Another embodiment uses a radio-opaque substrate for the elastic material so that the dissecting progress can be monitored using x-ray equipment. Further, radio-opaque markers are positioned in certain embodiments to assist in identifying position and orientation of the dissector during use.

When proper dissection is completed, in the preferred procedure, the balloon is allowed to remain at its maximum inflated state for a few minutes before the medium is withdrawn. This minimizes bleeding in the dissected site. The withdrawal of the medium deflates the elastic balloon and the dissector is easily removed.

This dissection permits a subsequent surgical procedure to be performed at the site. In the field of cosmetic surgery, this subsequent procedure may the implanting of a variety of implantable devices such as: breast augmentation implants; malar implants; chin implants; and calf implants. Even further, the dissection is useful for the creation of tissue flaps used in a variety of surgical procedures.

Since the tube is rigid, one end of the tube is preferably shaped as a dissector. A blunt dissector shape is the preferred shape permitting tho balloon dissector to be inserted through its own dissecting path. Once in proper position, the tube then serves the purpose of conveyance of the medium to the elastic balloon.

In one application of the invention, the tube is partially inserted and the balloon is inflated. This inflation dissects the immediate area. The medium is removed, thereby deflating the elastic balloon; and the tube is pushed further into the patient to a new dissection site where the balloon is again inflated and then deflated. This approach allows the surgeon to gradually move through an area and create a channel of dissected tissue.

The rigid tube is graspable by the surgeon and is used as an instrument during its insertion into the site. The tube is gripped at its base end by the surgeon. Although some embodiments create a "grip shape" in the tube, others simply provide a smooth and extended surface for the surgeons grasp.

The griping portion, as used in some embodiments of the invention, provides the surgeon with the ability to easily manipulate the tube into proper position.

The rigid tube, in one embodiment of the invention, is rigidly affixed to a syringe containing the medium so that the syringe/tube combination form one unit which is manipulated by the surgeon. In this embodiment, the dissecting tube of this invention becomes an extension of the syringe itself.

In this embodiment, the surgeon is able to grasp the syringe for probing and manipulation of the dissector. When the dissector is properly positioned, the surgeon depresses the plunger on the syringe to force the medium through the tube to inflate the balloon and perform the dissection.

In this context, the use of a toomey type of connector for the syringe is preferred as the toomey type of connector gives excellent mechanical stability to the dissector.

The shape of the inflated balloon dissector is controlled by the manufacture of the elastic balloon as well as the amount of inflation applied to the elastic balloon.

Through the use of ribs and by varying the thickness of the walls of the elastic balloon, a shape is defined during the manufacture of the dissector.

The amount of inflation is further defined, in one embodiment of the invention, by including in the kit, a syringe for inflation. The syringe is "pre-loaded" with a defined volume. In this manner, the surgeon is assured that the balloon will be inflated to the proper volume.

In the same fashion, one embodiment of the invention provides the proper volume of liquid or gel for the inflation of the implant.

The invention, together with various embodiments thereof, will be more fully explained by the attached drawings and the following descriptions.

DRAWINGS IN BRIEF

FIGS. 3A, 3B, 3C, and 3D illustrate the use of the preferred embodiment in a typical surgical procedure, the dissection of breast tissue for a breast augmentation procedure.

Figure 4A:
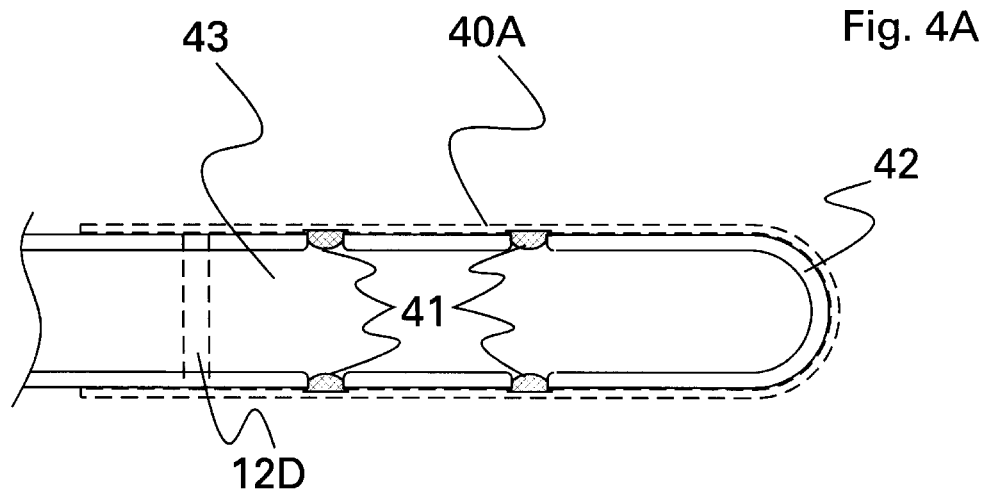
Figure 4B:
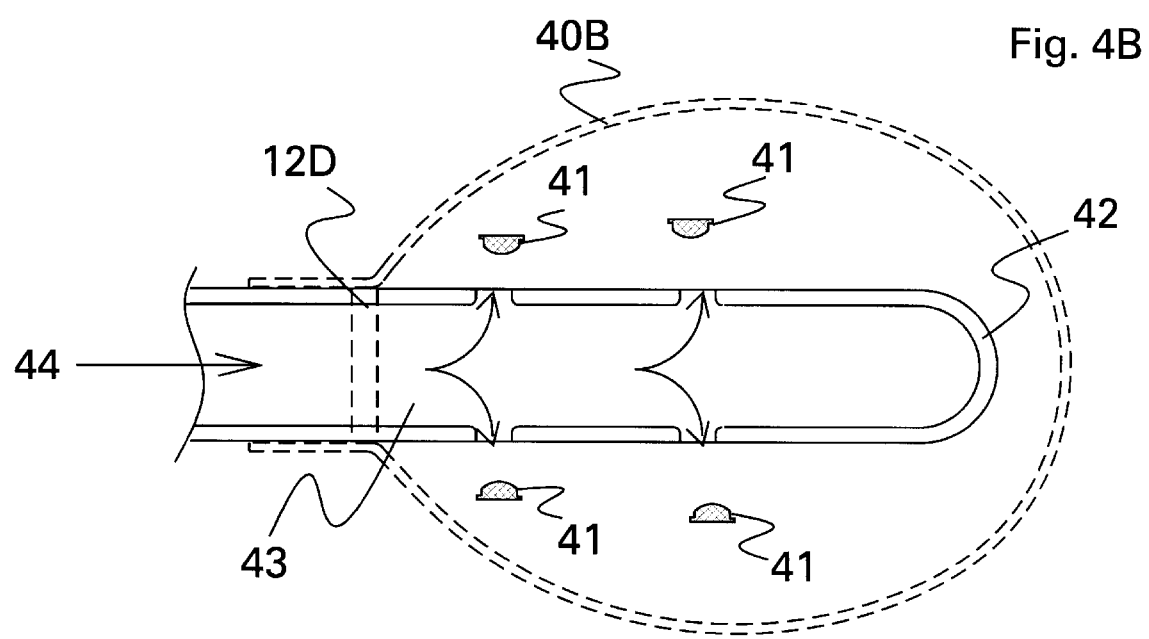

FIGS. 4A and 4B illustrate the use of plugs to seal the hollow rigid tube and the plugs ejection during the dissection procedure.

Figure 5:
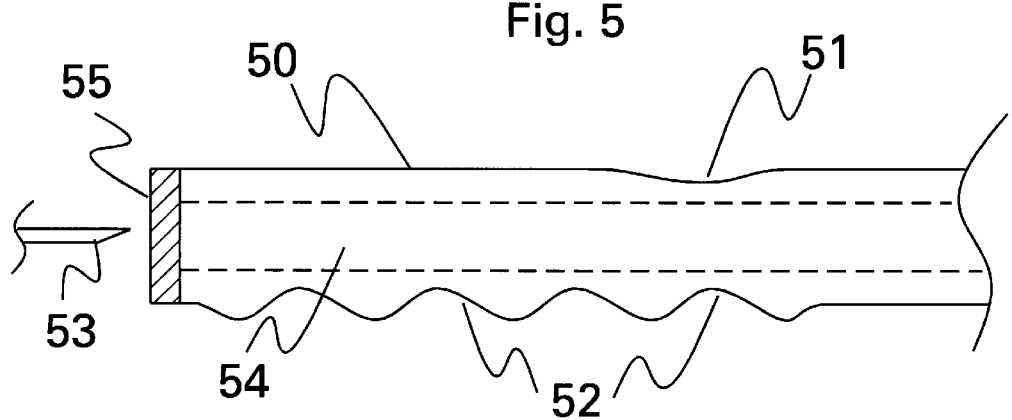

FIG. 5 is a side view of an embodiment of the invention illustrating an embodiment of the grip used in some embodiments of the invention and the use of a needle/syringe for inflation of the elastic balloon.

Figure 6:
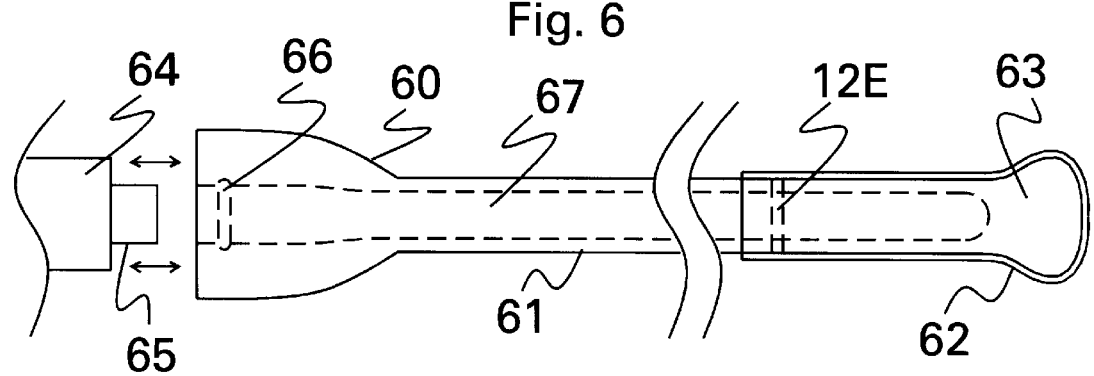

FIG. 6 is a side view of an embodiment of the invention in which the dissector is mountable onto a syringe.

Figure 7:
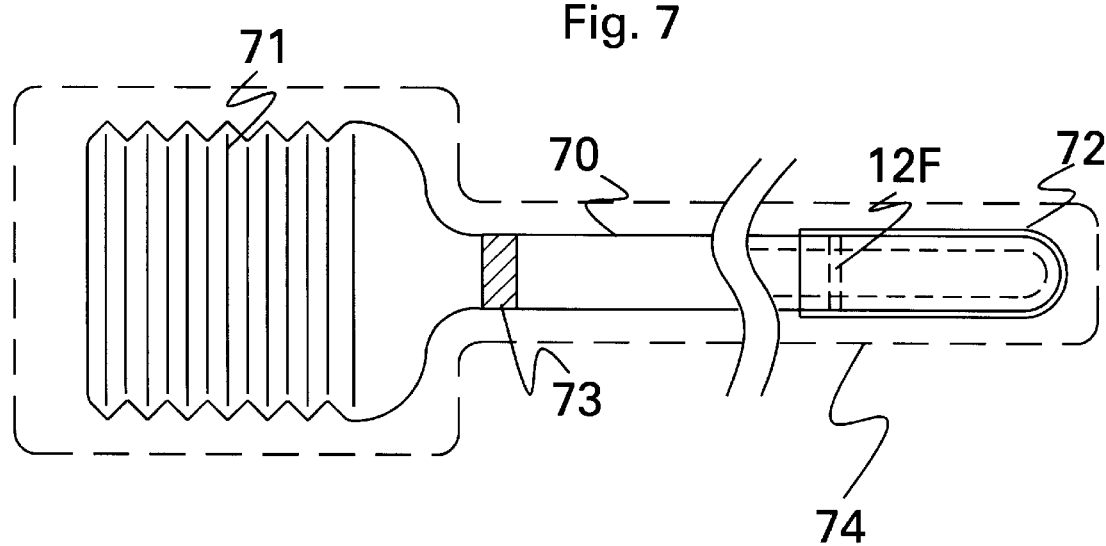

FIG. 7 is a side view of an embodiment of the invention in which a bellows is used for the inflation of the elastic balloon.

FIGS. 8A, 8B, 8C, and 8D illustrate the preferred manufacturing steps for creation of the present invention.

FIGS. 9A–F illustrate the steps taken in utilizing this invention for the dissecting and positioning of the implant within the patient.

Figure 10A:
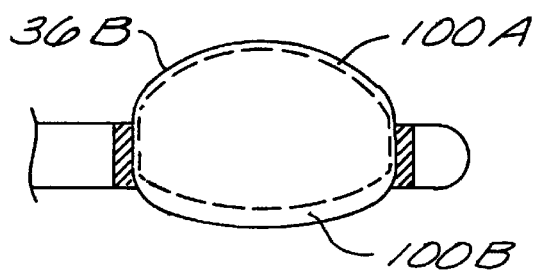
Figure 10B:
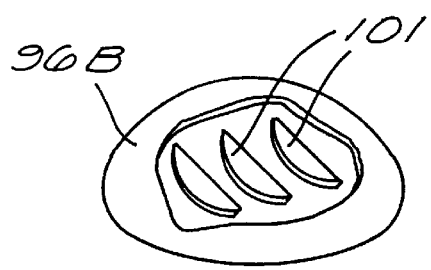

FIGS. 10A and 10B illustrate the preferred technique for forming a shape in the dissecting balloon and the implant.

Figure 11:
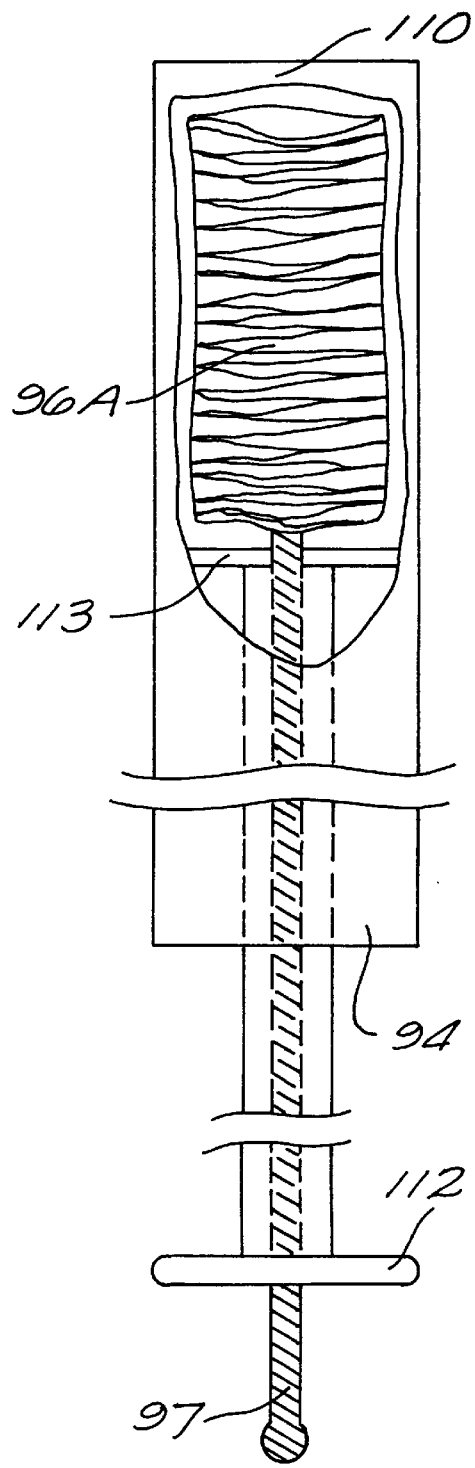

FIG. 11 is a cut-away view of the preferred instrument used for the placement of the implant.

Figure 12:
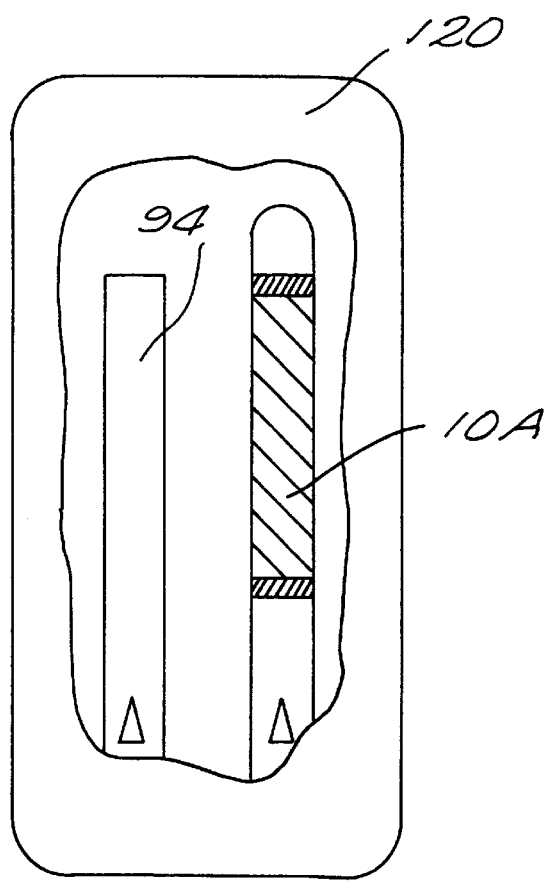

FIG. 12 graphically illustrates one embodiment of the present invention's kit.

Figure 13:
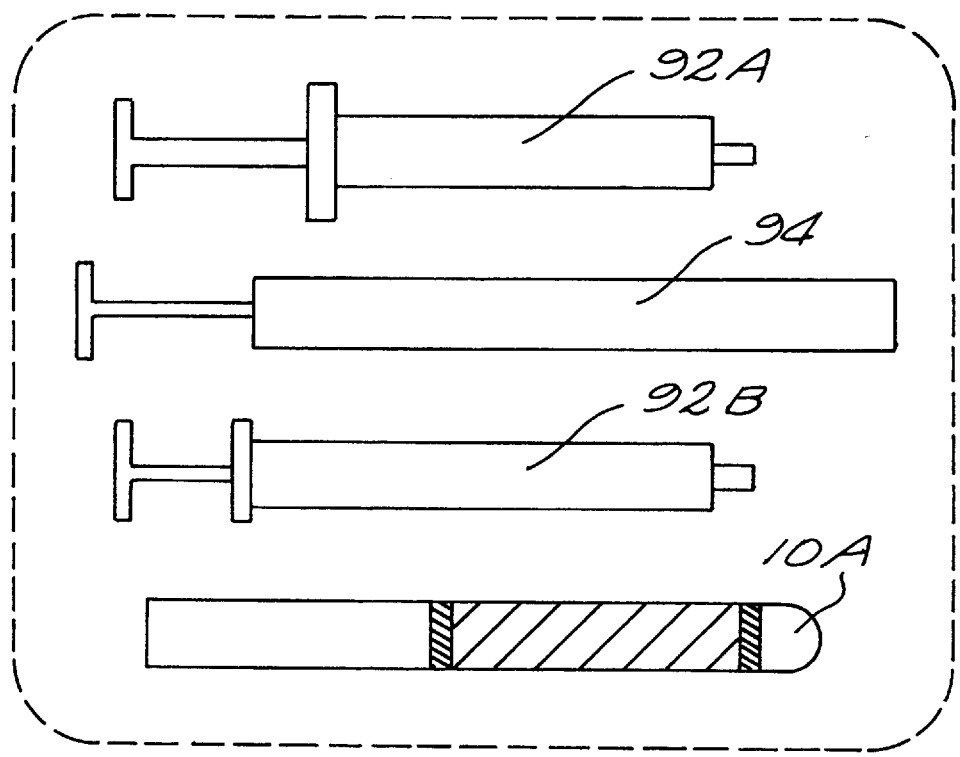

FIG. 13 illustrates an alternative embodiment of a kit of the present invention.

DRAWINGS IN DETAIL

Figure 1A:
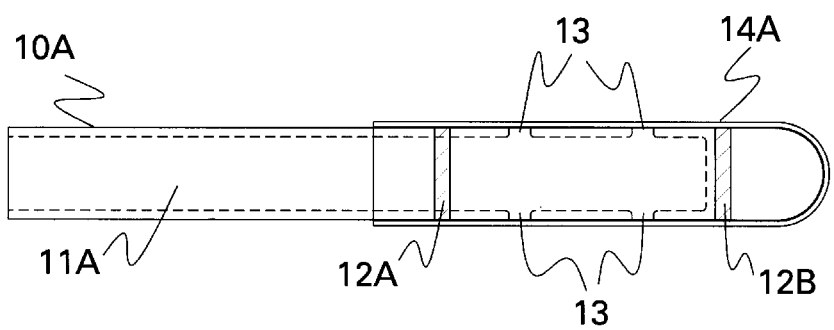
FIGS. 1A and 1B illustrate the preferred embodiment of the invention in its insertion/withdrawal state and in its dissecting state.
Figure 1B:
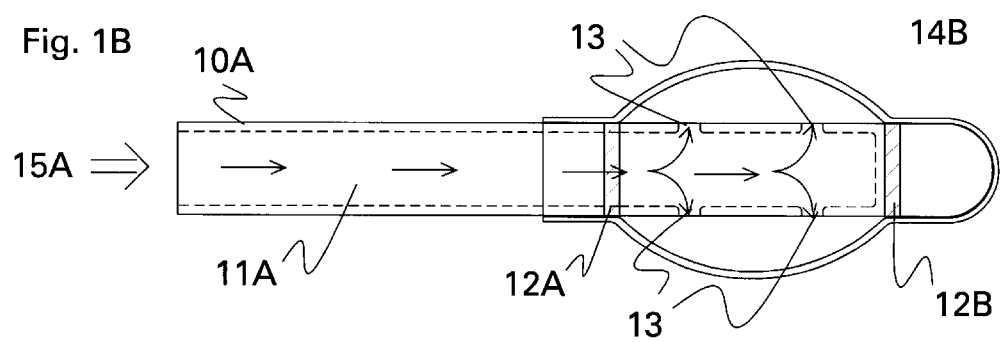

FIGS. 1A and 1B illustrate the preferred embodiment of the invention in its insertion/withdrawal state and in its dissecting state.

Referring to FIG. 1A, rigid tube 10A has an interior channel 11A which, in this embodiment, extends partially through the length of rigid tube 10A. Exit ports 13 communicate the interior of hollow tube 10A with its exterior.

An elastic material is placed over the end of rigid tube 10A to form balloon 14A. This elastic material is secured to rigid tube 10A through the use of anchors 12A and 12B. A releasing agent, not shown, is placed around the exterior of rigid tube 10A between anchors 12A and 12B. The releasing agent prevents the elastic material 14A from bonding with the rigid tube in this area.

Those of ordinary skill in the art readily recognize a variety of elastic materials and releasing agents which can be used in this context. The preferred material used for the rigid tube is surgical steel, but, those of ordinary skill in the art readily recognize that alternative materials are useable in this context including hardened plastic.

The elastic material bonds anchors 12A and 12B with the exterior of rigid tube 10A.

As shown in FIG. 1B, as a medium 15A is introduced into channel 11A of rigid tube 10A, the medium escapes through exit ports 13 to inflate the elastic material as dissecting balloon 14B.

Note, no sheath is used in this invention as the balloon is used directly with the rigid tube which serves as a probe, guide, and conduit for the medium.

Figure 2A:
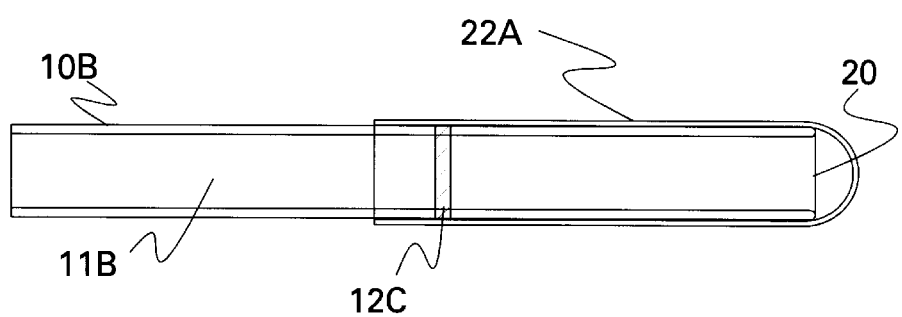
FIGS. 2A and 2B illustrate an alternative embodiment of the invention in its insertion/withdrawal state and in its dissecting state.
Figure 2B:
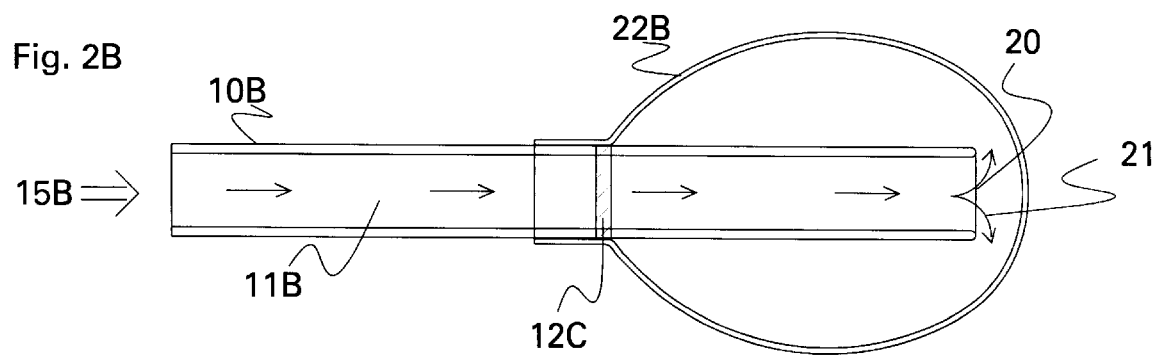

FIGS. 2A and 2B illustrate an alternative embodiment of the invention in its insertion/withdrawal state and in its dissecting state.

FIG. 2A illustrates the state of the balloon dissector which is used for either insertion or withdrawal of the dissector from the surgical site. In this embodiment, rigid tube 10B has a channel 11B extending the entire length of rigid tube 10B with an exit port 20.

Anchor 12C provides a bonding mechanism between elastic material 22A and the exterior of rigid tube 10B. As with the anchors discussed earlier, anchor 12C provides a "boundary" for the inflated elastic material, keeping the elastic material within a pre-defined range.

In this embodiment, a releasing agent (not shown) is placed around the tip of rigid tube 10B to keep elastic material 22A from bonding with the elastic material. The releasing agent is only applied up to anchor 12C.

Medium 15B, as shown in FIG. 2B, is introduced into the rigid tube 10B and is communicated through channel 11B to cause the elastic material to inflate into balloon 22B. This selective inflation into balloon 22B permits the surgeon to dissect the surgical site.

FIGS. 3A, 3B, 3C, and 3D illustrate the use of the preferred embodiment in a typical surgical procedure, the dissection of breast tissue for a breast augmentation procedure.

Figure 3A:
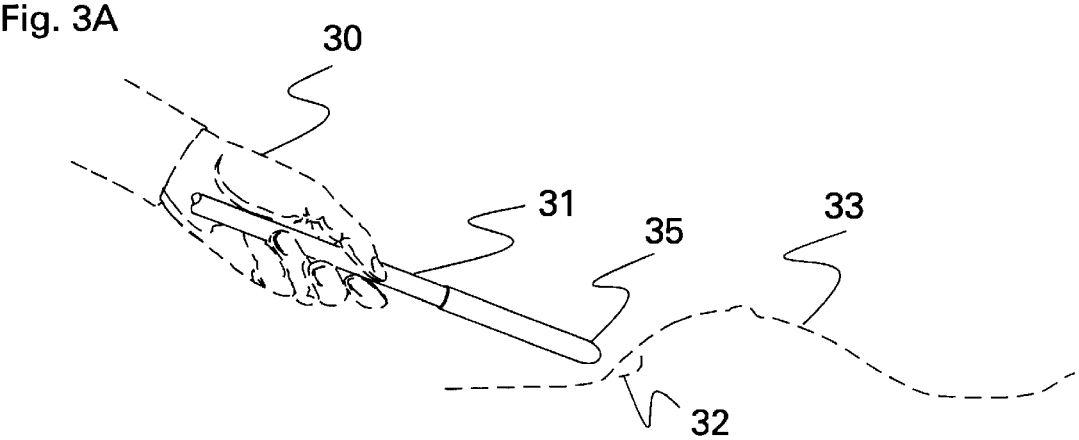

In FIG. 3A, incision 32 is created in patient 33 and surgeon 30 grasps dissector 31 for insertion through incision 32. End 35 of dissector 31 is shaped to assist in performing blunt dissection during the insertion of dissector 31 into patient 33.

Figure 3B:
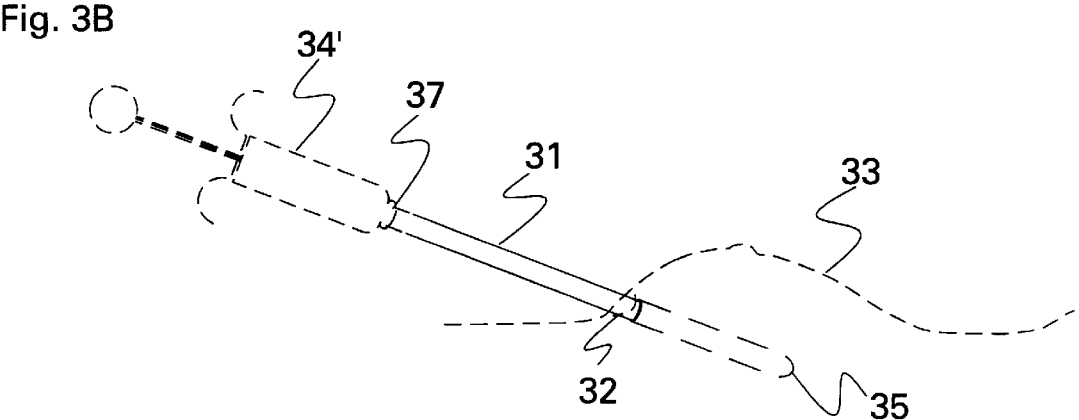
Figure 3C:
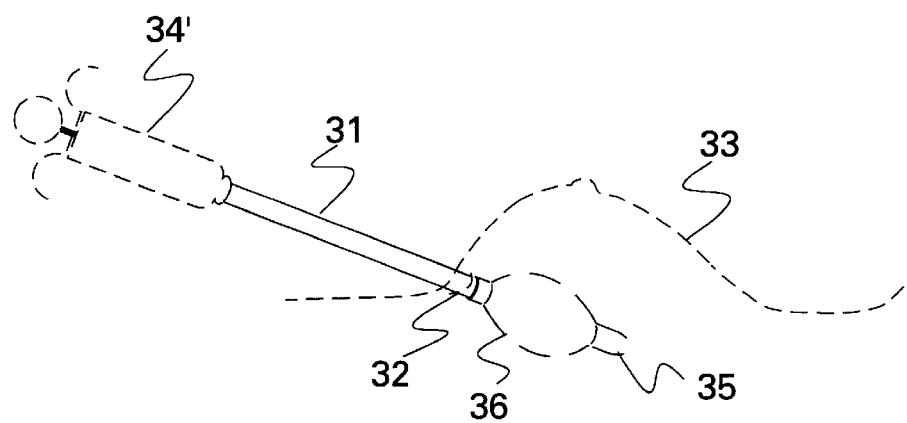

Once dissector 31 has been inserted so that end 35 is in the proper position, FIG. 3B, syringe 34 is inserted into end 37 of dissector 31. Syringe 34A contains the medium which is to be used for inflation of the balloon dissector.

The contents of the syringe 34 is pressed into dissector 31 causing balloon 36 to inflate and dissect in the desired area. In the preferred embodiment, balloon 36 is maintained in a full condition for a two or more minutes to minimize bleeding within the site once dissector 31 is removed.

Figure 3D:
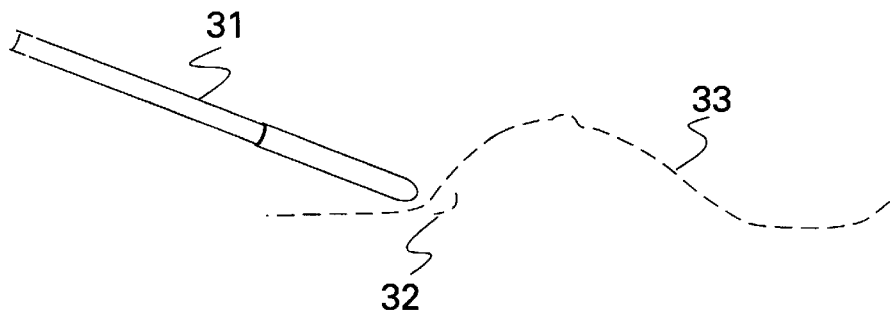

FIG. 3D illustrates the removal of dissector 31 leaving the surgical site prepared for subsequent procedures.

FIGS. 4A and 4B illustrate the use of plugs to seal the hollow rigid tube and the plugs ejection during the dissection procedure.

In some embodiments, the use of plugs is advantageous both in the manufacturing process and when a medium is stored within the rigid tube prior to the use of the dissector.

Prior to use, as illustrated in FIG. 4A, plugs 41 seal the exit ports formed in the walls of channel 43 within rigid tube 42. Located on an exterior surface of rigid tube 42 is elastic material 40A which is bonded to the rigid tube at anchor 12D.

In this embodiment of the invention, a medium is stored within channel 43.

FIG. 4B illustrates the results of pressure 44 being applied to the medium within channel 43. The increased pressure forces plugs 41 to be ejected from the exit ports permitting the medium to inflate the elastic material into dissecting balloon 40B.

While the present invention illustrates the use of four plugs, any number of plugs and exit ports may be employed in the present invention. Those of ordinary skill in the art recognize that the number and size of the exit ports and plugs are determined by the parameters and capabilities of the dissector sought.

In other embodiments, soluble plugs are used which dissolve upon contact with the medium being injected into the tube.

FIG. 5 is a side view of an embodiment of the invention Illustrating an embodiment of the grip used in some embodiments of the invention and the use of a needle/syringe for inflation of the elastic balloon.

While the embodiment illustrated in FIGS. 3A–D illustrate the use of a straight grip on the dissector, the embodiment of FIG. 5 has configured rigid tube 50 with a thumb indentation 51 as well as finger grips 52. These arrangements provide for a more secure grasp by the surgeon.

This embodiment also provides for a rubber seal 55 which protects channel 54 until syringe needle 53 punctures rubber seal 55. Syringe needle 53 is used to inject medium into channel 54 to inflate the balloon dissector (not shown).

Additionally, some embodiments which utilize this shape have a layer of elastic material totally covering the dissector. No releasing agent is applied in the handle/grip area so the elastic material bonds directly with the rigid tube 50 and provides exceptional frictional contact with the surgeon's hand.

FIG. 6 is a side view of an embodiment of the invention in which the dissector is mountable onto a syringe using a toomey-type of arrangement.

In this embodiment, rigid tube 61 is mounted onto connector 60. Connector 60 is a toomey-style of connector permitting it to be rigidly attached to nozzle 65 of syringe 64. This rigid attachment provides the surgeon with an extension, syringe 64, for manual manipulation of balloon dissector.

Seal 66 is punctured by nozzle 65 during attachment of connector 60 with syringe 64. Seal 66 is used to maintain a sterile condition and medium within channel 67.

The combination of syringe 64 with rigid tube 61, form a complete balloon dissector permitting the syringe to be discharged into rigid tube 61 to flow through and inflate balloon 62. Again, anchor 12E is used to assist in defining the limit of the balloon's expansion.

End 63 of tube 61, in this embodiment, is configured to assist in blunt dissection during insertion of the balloon dissector into the surgical site.

For small dissectors, the use of a luer-lock connector is sufficient in this context.

FIG. 7 is a side view of an embodiment of the invention in which a bellows is used for the inflation of the elastic balloon.

Bellows 71 is secured to rigid tube 70 at collar 73. A medium is stored within bellows 71 and the interior of rigid tube 71. When the elastic material 72 is properly positioned within the patient, the surgeon squeezes and holds bellows 71 to inflate elastic material 72, thereby performing the dissection of the tissue. Anchor 12F provides a bond between rigid tube 70 and elastic material 72.

When the dissector is to be removed, the surgeon releases bellows 71, which is adapted to naturally re-inflate, and the medium is withdrawn into bellows 71, thereby collapsing elastic material 72.

Use of the dissector requires that the surgeon remove packaging 73 which contains the dissector in a sterile environment. Once the dissector has been used, the dissector is disposed to prevent contamination.

FIGS. 8A, 8B, 8C, and 8D illustrate the preferred manufacturing steps for creation of the present invention.

Figure 8D:
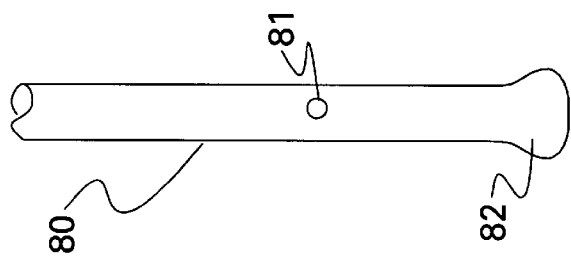
Figure 8C:
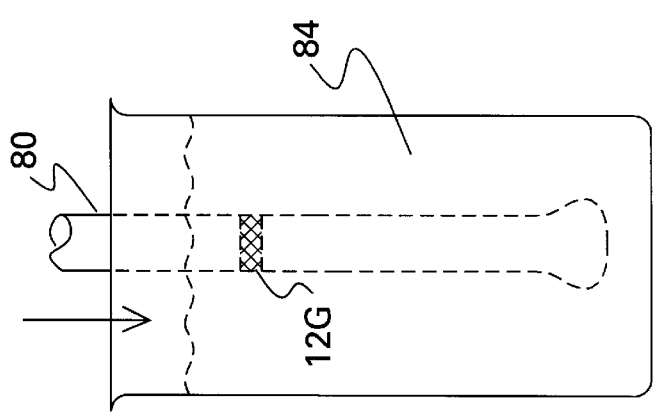
Figure 8B:
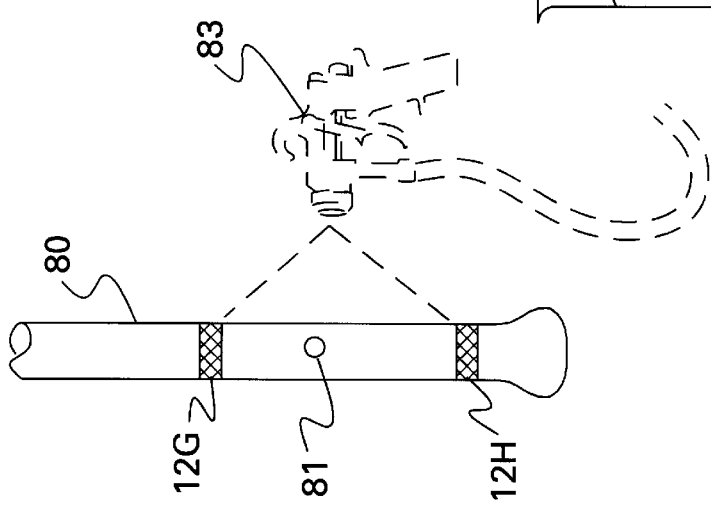
Figure 8A:
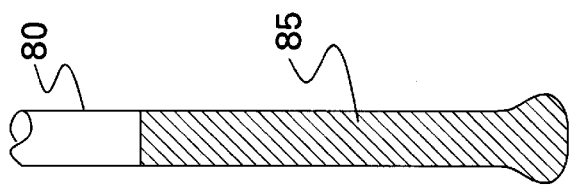

As shown in FIG. 8A, rigid tube 80 has its end 82 configured to serve as a dissector. Hole and plug 81 have been formed in rigid tube 80.

In FIG. 8B, anchors 12G and 12H have been applied around the circumference of the rigid tube 80 on both sides of hole and plug 81. A releasing agent 83 is applied between anchors 12G and 12H.

FIG. 8C shows the rigid tube 80 being dipped into liquid elastic material 84 so that anchor 12G is submerged therein. This dipping and then its removal, as shown in FIG. 8D, form a layer of elastic material 85 around the end of rigid tube 80. In the preferred embodiment, elastic material 85 is a silicone elastomer.

In this manner, the balloon dissector of the present invention is easily manufactured at a minimum of costs.

In some embodiments, a stiff member is added to the elastic material to form a cutting dissector on the expanding material and also to define a shape and contour of the balloon during expansion.

FIGS. 9A–F illustrate the steps taken in utilizing this invention for the dissecting and positioning of the implant within the patient.

In FIG. 9A, after an incision has been made in the skin layer, balloon dissector 10A is inserted into the patient. Indicia 90A provides the surgeon with proper orientation of dissector 10A.

Dissector 10A, in this illustration has two anchors 12A and 12B with an expandable membrane or balloon 36A interposed therebetween.

Once proper positioning is obtained, FIG. 9B, syringe 92A is secured to the end of dissector 10A and a sterile fluid is injected, as shown by arrow 93A, into balloon 36B causing balloon 36B to expand and dissect the surrounding tissue.

Once the dissection has been accomplished, FIG. 9C, syringe 92A withdraws, as indicated by arrow 93B, the liquid causing the balloon to collapse to its original condition 36A. Dissector 10A is then removed.

As shown in FIG. 9D, implant sheath 94 is inserted through the incision in the skin so that the end of implant sheath 94 is properly positioned. Orientation of the implant is facilitated by indicia 90B.

The collapsed implant is then pushed from implant sheath 94 into the dissected area.

Tube 97A runs from implant 96A, FIG. 9E, outside the incision and is accessible to syringe 92B which is connected to tube 97A as indicated by arrows 93D and a fluid or gel is pushed, as indicated by arrow 93C, into the interior of implant 96A to cause it to expand.

Once expanded, tube 97A is severed 95, and the port sealed. The excess tube 97B, illustrated in FIG. 9F, is withdrawn from the surgical site leaving the fully inflated implant 96B.

FIGS. 10A and 10B illustrate the preferred technique for forming a shape in the dissecting balloon and the implant.

The shape of dissector 36B is partially defined in the manufacturing process by varying the wall thickness. As shown wall portion 100A is significantly narrower than wall portion 100B. This difference in the wall width causes the dissector to take on a pre-chosen shape.

In a complimentary fashion, the shape of implant 96B mirrors the shape of dissector 36B. In this illustration, implant 96B has its outer shape defined through the use of ribs 101 formed within the implant.

While these two techniques (wall width and ribbing) are capable of assisting in defining the shape of the dissector and implant, those of ordinary skill in the art readily recognize a variety of other techniques which will serve this function.

FIG. 11 is a cut-away view of the preferred instrument used for the placement of the implant.

Implant tube 94 contains the collapsed implant 96A. When the surgeon is ready to discharge the implant into the site, plunger 112 is pressed, forcing ram 113 to press the collapsed implant 96A into the surgical site.

Inflation tube 97, in this embodiment, extends through the center of plunger 112 and ram 113. Once the collapsed implant 96A has been discharged, the surgeon is able to inflate the implant using inflation tube 97 as outlined above.

FIG. 12 graphically illustrates one embodiment of the present invention's kit.

In the embodiment of this figure, kit 120 holds a balloon dissector 10A as well as the implant mechanism 94. As discussed before, the balloon dissector 10A is matched to the implant.

FIG. 13 illustrates an alternative embodiment of a kit of the present invention.

In this embodiment, kit 130, forming a sterile environment, contains balloon dissector 10A as well as implant mechanism 94. Further, syringe 92A is also enclosed within kit 130. Syringe 92A is pre-charged with the proper amount of liquid to obtain the dissection sought to meet the requirements of the specific implant.

Also included within kit 130 is syringe 92B which is also pre-charged with the proper amount of liquid/gel to fully inflate the implant.

Kit 130 provides all of the mechanisms for the surgeon to properly dissect and implant.

It is clear that the present invention creates a highly improved implant kit for use in a variety of surgical settings.

What is claimed is:

1. A surgical kit comprising:
   a) surgical dissector having,
      1) a hollow rigid tube having a first end adapted to receive a flowing medium and an opening located proximate to a second end of said hollow rigid tube,
      2) two anchors positioned on each side of said opening in said hollow rigid tube, each of said anchors totally encircling said hollow rigid tube and bonded to said hollow rigid tube, 3) an elastic expandable balloon being secured to said two anchors, an interior portion of said expandable balloon in communication with an interior portion of said hollow rigid tube, said elastic expandable balloon having a predefined shape, and
4) a film interposed between said expandable balloon and said hollow rigid tube between said two anchors, said film adapted to prevent said elastic expandable balloon from bonding to said hollow rigid tube; and, b) a deflated surgical implant, said deflated surgical implant having, when inflated, a shape complimentary to the predefined shape of said elastic expandable balloon.

2. The surgical kit according to claim 1, wherein said deflated surgical implant includes insertion means adapted to position said deflated surgical implant in a space created within a patient by said surgical dissector.

3. The surgical kit according to claim 2, wherein said deflated surgical implant includes a portal adapted to communicate a liquid medium to an interior of said deflated surgical implant.

4. The surgical kit according to claim 3, further including means for sealing said portal after said liquid medium has been communicated to the interior of said deflated surgical implant.

5. The surgical kit according to claim 2,
a) wherein said surgical dissector includes a first orientation indicia imprinted on a proximal end of said hollow rigid tube; and,
b) wherein said insertion means includes a second orientation indicia thereon.

6. The surgical dissector according to claim 1, further including means for rigidly connecting the first end of said hollow rigid tube to a syringe.

7. The surgical dissector according to claim 6, further including a seal over the first end of said hollow rigid tube, said seal adapted to be broken by attachment of said means for rigidly connecting the first end of said hollow rigid tube to a syringe.

8. The surgical dissector according to claim 1, wherein said first end of said hollow rigid tube is sealed and is adapted to be punctured by a needle from a syringe.

9. An implant kit comprising:
a) a balloon dissector having,
1) a hollow rigid tube having a first end adapted to receive a flowing medium and an opening proximate to a second end thereof,
2) an elastic balloon being secured to said hollow rigid tube such that said elastic balloon encloses the opening in said hollow rigid tube, said elastic balloon having a defined shaped when inflated,
3) an anchor positioned between the first and second end of said hollow rigid tube, said anchor totally encircling said hollow rigid tube and bonded to said hollow rigid tube and said elastic balloon, and,
4) a film interposed between said elastic balloon and said hollow rigid tube between the second end and said anchor, said film adapted to prevent said elastic balloon from bonding to said hollow rigid tube; and, b) a deflated surgical implant, said deflated surgical implant having, when inflated, a shape complimentary to the defined shape of said elastic balloon.

10. The implant kit according to claim 9, wherein said deflated surgical implant includes insertion means adapted to position said deflated surgical implant within a space created within a patient by said surgical dissector.

11. The implant kit according to claim 10, wherein said deflated surgical implant includes a portal adapted to communicate a liquid medium into an interior of said deflated surgical implant.

12. The implant kit according to claim 11, further including means for sealing said portal after said liquid medium has been communicated to the interior of said deflated surgical implant.

13. The implant kit according to claim 10,
a) wherein said surgical dissector includes a first orientation indicia imprinted on a proximal end of said hollow rigid tube; and,
b) wherein said insertion means includes a second orientation indicia thereon.

14. A kit comprising:
a) a dissector having,
1) a hollow rigid tube having,
A) a first end adapted to receive a flowing medium, and,
B) a second end adapted to dissect tissue, said second end having an opening proximate thereto for communication of medium from an interior of said hollow rigid tube,
C) a grip portion located proximate to the first end and adapted for manual manipulation of said hollow rigid tube, and,
2) an expandable balloon being secured proximate to a second end of said hollow rigid tube and on an exterior portion thereof, an interior portion of said expandable balloon in liquid communication with an interior portion of said hollow rigid tube,
3) two anchors positioned on each side of said opening in said hollow rigid tube, each of said anchors totally encircling said hollow rigid tube and bonded to said hollow rigid tube and said expandable balloon, and,
4) a film interposed between said expandable balloon and said hollow rigid tube between said two anchors, said film adapted to prevent said expandable balloon from bonding to said hollow rigid tube;
b) means for,
1) inserting a first sterile liquid medium into said expandable balloon, and,
2) withdrawing said first sterile liquid medium from said expandable balloon;
c) a deflated surgical implant, said deflated surgical implant having, when inflated, a shape complimentary to the predefined shape of said elastic expandable balloon;
d) insertion means for positioning said deflated surgical implant within a space created within a patient by said surgical dissector; and,
e) means for inserting a second sterile liquid medium into said deflated surgical implant.

15. The kit according to claim 14,
a) wherein said deflated surgical implant includes a portal adapted to communicate a liquid medium into an interior of said deflated surgical implant; and,
b) further including means for sealing said portal after the liquid medium has been communicated into the interior of said deflated surgical implant.

16. The kit according to claim 14,
a) wherein said surgical dissector includes a first orientation indicia imprinted on a proximal end of said hollow rigid tube; and,
b) wherein said insertion means includes a second orientation indicia thereon.

17. A kit comprising:
a) a hollow rigid tube having a first end adapted to receive a flowing medium and an opening proximate to a second end thereof;
b) an expandable balloon being secured to said hollow rigid tube such that said expandable balloon encloses the opening in said hollow rigid tube; and,
c) a deflated surgical implant, said deflated surgical implant having, when inflated, a shape complimentary to the predefined shape of said elastic balloon.

18. The kit according to claim 17, wherein said deflated surgical implant includes insertion means adapted to position said deflated surgical implant within a space created within a patient by said surgical dissector.

19. The kit according to claim 18,
a) wherein said deflated surgical implant includes a portal adapted to communicate a liquid medium into an interior of said deflated surgical implant; and,
b) further including means for sealing said portal after said liquid medium has been communicated into the interior of said deflated surgical implant.

20. The kit according to claim 19,
a) wherein said surgical dissector includes a first orientation indicia imprinted on a proximal end of said hollow rigid tube; and,
b) wherein said insertion means includes a second orientation indicia thereon.

* * * * *